United States Patent [19]

De Barbieri

[11] Patent Number: 4,666,887

[45] Date of Patent: * May 19, 1987

[54] INTRAVENOUS OR INTRAPERITONEAL ADMINISTRATION OF A TRIPEPTIDE COMPOUND FOR TREATING CANCER

[75] Inventor: Augusto De Barbieri, Milan, Italy

[73] Assignee: Proter S.p.A., Opera, Italy

[*] Notice: The portion of the term of this patent subsequent to Apr. 2, 2002 has been disclaimed.

[21] Appl. No.: 626,938

[22] Filed: Jul. 2, 1984

Related U.S. Application Data

[63] Continuation of Ser. No. 445,583, Nov. 30, 1982, abandoned, which is a continuation-in-part of Ser. No. 311,646, Oct. 15, 1981, Pat. No. 4,428,875, which is a continuation-in-part of Ser. No. 173,621, Jul. 30, 1980, Pat. No. 4,314,999, which is a continuation-in-part of Ser. No. 929,327, Jul. 31, 1978, Pat. No. 4,216,208.

[51] Int. Cl.⁴ .............................................. A61K 35/02
[52] U.S. Cl. ...................................... 514/18; 530/331
[58] Field of Search ................. 424/177; 260/112.5 R; 530/331; 514/18

[56] References Cited

U.S. PATENT DOCUMENTS

| | | | |
|---|---|---|---|
| 4,087,520 | 5/1978 | Bran et al. | 260/112.5 R |
| 4,127,534 | 11/1978 | Coy et al. | 424/177 |
| 4,153,688 | 5/1979 | Dimicoli et al. | 260/112.5 R |

*Primary Examiner*—Blondel Hazel
*Attorney, Agent, or Firm*—Fisher, Christen & Sabol

[57] ABSTRACT

A pharmaceutical composition for use in the treatment of malignant tumor cells in laboratory animals is disclosed. The pharmaceutical composition uses a pharmaceutically acceptable excipient with a tripeptide compound as the active ingredient. The tripeptide compound is formed from dichlorodiethylaminophenylalanine, parafluorophenylalanine, and methione.

5 Claims, No Drawings

INTRAVENOUS OR INTRAPERITONEAL ADMINISTRATION OF A TRIPEPTIDE COMPOUND FOR TREATING CANCER

RELATED APPLICATIONS

This is a continuation of application Ser. No. 445,583, filed on Nov. 30, 1982 (abandoned); which is a continuation-in-part of application Ser. No. 311,646, filed Oct. 15, 1981 now U.S. Pat. No. 4,428,875; which is a continuation-in-part of application Ser. No. 173,621, filed July 30, 1980 and now U.S. Pat. No. 4,314,999; which is a continuation-in-part of application Ser. No. 929,327 filed July 31, 1978 and now U.S. Pat. No. 4,216,208.

BACKGROUND OF THE INVENTION

(1) Field of the Invention

The present invention relates to chemotherapeutic tripeptide compounds consisting of dichlorodiethylaminophenylalanine, parafluorophenylalanine, and methionine covalently linked which are useful in the treatment of tumor cells. The present invention also relates to a process for preparation and to a process for administration of the chemotherapeutic compounds.

The present invention also provides pharmaceutical compositions which contain at least one of the new tripeptide compounds in admixture with a solid or liquid pharmaceutical carrier that is physiologically acceptable.

The present invention then relates to chemotherapy against tumor of animals by administering the various chemotherapeutic compounds to test animals by intravenous or intraperitoneal or by oral route.

(2) Prior Art

Chemotherapy as been and still is an object of intense research. Certain positive results have undoubtedly been achieved, especially by means of polychemotherapy realized by associating different active substances according to carefully developed protocols. However, the ideal therapy has not been found. The need to find new active substances has been particularly emphasized. All the foregoing justifies continuous research directed toward preparing new chemotherapeutic compounds active against cancerous tumors. There are already known peptides having anti-tumor activity, consisting of both normal and antimetabolic amino acids, coupled by means of a peptide bond. Such peptides have for years been in therapeutic use with favorable results both in monochemotherapy and in polychemotherapy.

The amino acid dichlorodiethylaminophenylalanine which contains the —N(CH$_2$CH$_2$Cl)$_2$ group in the meta-position of the benzene ring displays for certain tumors greater activity than the para-compound. The highly active ortho-derivative is the least stable and the most toxic of the three isomers.

SUMMARY OF THE INVENTION

The compounds of the present invention are based on the discovery that a tripeptide can be manufactured by bonding the amino acid dichlorodiethylaminophenylalanine by peptide links to parafluorophenylalanine and methionine which is highly effective against cancerous tumors and is considerably less toxic than dichlorodiethylaminophenylalanine.

For purposes of simplification, the amino acid dichlorodiethylaminophenylalanine having the structural formula:

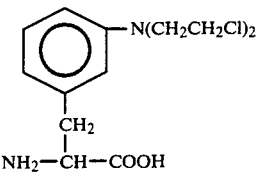

in which the —N(CH$_2$CH$_2$Cl)$_2$ group can be in the ortho, meta, or paraposition, with the meta-position preferred. This structure is indicated by MPhe.

The amino acid parafluorophenylalanine having the structural formula:

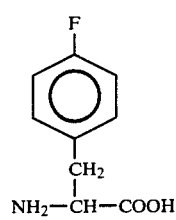

is indicated by pFPhe.

The amino acid methionine of the formula:

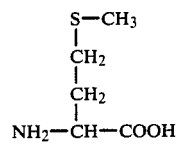

is indicated by Met.

Applicants have discovered that the tripeptides formed from the above three specified amino acids have chemotherapeutic activity against malignant tumors but are less toxic than dichlorodiethylaminophenylalanine itself. As a result thereof, the present invention provides a new family of six anti-tumor compounds relating to all permutations of the three amino acids:

1. pFPhe.MPhe.Met.
2. pFPhe.Met.MPhe.
3. MPhe.pFPhe.Met.
4. MPhe.Met.pFPhe.
5. Met.pFPhe.MPhe.
6. Met.MPhe.pFPhe.

The three amino acids of each antitumor compound have a laevo-rotatory (L) configuration in all the sequences specified above.

Each of the three amino acids, dichlorodiethylaminophenylalanine, parafluorophenylalanine, and methionine have an amine (—NH$_2$) group at one end of the amino acid chain and a carboxyl group (—COOH) at the opposite end. The amino acids are coupled together by the formation of peptide links (—CONH—), which result when the carboxyl group of one of the amino acids couples with an amine group of another amino acid. When the three amino acids are coupled together, forming a tripeptide, there still remains one amine group and one carboxyl group at opposite ends of the tripeptide.

The carboxyl group can be esterified with, for example, an ethyl radical (—C₂H₅). Reacting the carboxyl group with a base forms a salt of the tripeptide. Also, the ester of the tripeptide can be converted into an ester salt by reacting the ester with either an organic or inorganic acid. The preferred inorganic acid is hydrochloric acid, while the preferred organic acid is acetic acid.

In particular, the compounds of the present invention are prepared by protecting the terminal amine group of the amino acid or peptide by acylation to form a Schiff base by reaction with carbobenzoxy chloride or with formylchloride. The acylated amino acid or peptide is reacted with another amino acid having a blocked carboxyl group with the aid of dicyclohexylcarbodiimide, whereby condensation to form the peptide linkage (—CONH—) occurs. The terminal amine group is then deprotected by reagents which do not disturb peptide linkages. For example, deprotection may be achieved by catalytic hydrogenation or by hydrolysis with alcoholic hydrochloric acid. A third amino acid, prepared by protecting the terminal amine group of the amino acid or peptide, is then condensed with the above noted dipeptide with the aid of dicyclohexylcarbodiimide. In this way the acylated peptide is obtained. For the purpose of selectively protecting the amine functional groups, the amine group is acylated with, for example, formic acid or carbobenzoxy chloride. The carboxyl groups are protected by means of esterification to the methyl, ethyl, hexyl, or benzyl ester, which are then cleaved by cautious saponification. Of course, additional steps may be necessary to form ester or ester salts of the tripeptide compounds as stated previously. The following description will more fully describe the preparation of the tripeptides according to the synthesis specified above, and in particular will describe the preparation of a tripeptide ester salt.

DESCRIPTION OF THE PREFERRED EMBODIMENTS

Example 1

Synthesis of
N-[3-(p-fluorophenyl)-N-formyl-L-alanyl]-3-[m-bis(2-chloroethyl)aminophenyl]-L-alanine ethyl ester.
Dipeptide I by Reaction I

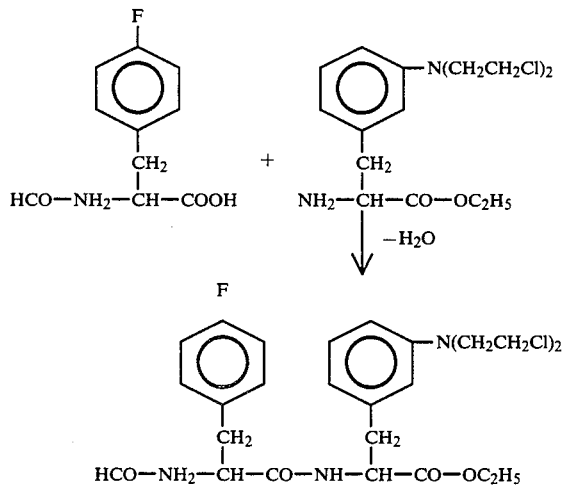

To m-bis(2-chloroethyl)aminophenyl-L-alanine ethyl ester [25.88 g] in 150 ml of tetrahydrofuran [15.37 g], 3-(p-fluorophenyl)-N-formyl-L-alanine [17.18 g] and of N,N-dicyclohexylcarbodiimide [15.85 g] were added successively while stirring for 15 minutes at 0° C. Temperature was then allowed to rise to 20° C. and the reaction mixture was kept under this condition for 5 hours. At the completion of the reaction, dicyclohexylurea was removed by filtration and the filtrate was evaporated at a reduced pressure at 40° C. Residue then was recovered by adding ethyl ether [150 ml] and the precipitate was recovered by filtration, and vacuum dried at 40° C. The raw substance was further purified by crystallization in 96% ethyl alchohol yielding a white crystalline substance (Dipeptide I) with MP 126°-7° C. Analysis showed a molecular composition of $C_{25}H_{30}FCl_2N_3O_4$ (M=526.44). The calculated molecular composition of the substance in %: C 57.04—H 5.74—N 7.98—Cl 13.47; and found %: C 56.88—H 5.71—N 8.01—Cl 13.32. The overall yield of the reaction was 73% Dipeptide I.

Synthesis of
N-[3-(p-fluorophenyl)-N-formyl-L-alanyl]-3-[m-bis(2-chloroethyl)aminophenyl]-L-alanine. Dipeptide II by Reaction II

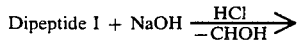

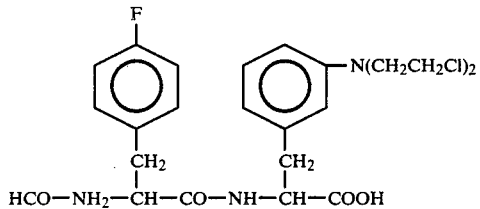

The white crystalline substance [26.3 g] (Dipeptide I) from reaction I was dissolved in acetone [130 ml] by gently heating at 40° C. After cooling it to room temperature, 50 ml of 1N NaOH was added while stirring for 1 hour at 20° C. The hydrolysis reaction was monitored with TLC using a mixture of ethyl alcohol/ethyl acetate/acetic acid: 50:50:1 (v/v/v) solvent system. At the completion of reaction, 50 ml of 1N HCl were slowly added. The white precipitate (Dipeptide II) thus formed was separated by filtration and washed with water until disappearance of Cl from the filtrate. The thus obtained substance was first air then vacuum dried. The white amorphous substance had the following characteristics: MP 103°-206° C. analysis showed a molecular composition of $C_{23}H_{26}FCl_2N_3O_4$ (M=498.39). The calculated composition in %: C 55.43—H 5.26—N 8.43—Cl 14.23; Found (%): C 55.17—H 5.24—N 8.47—Cl 14.81. The yield of reaction II was 95% of Dipeptide II.

Synthesis of
N-[N-[3-(p-fluorophenyl)-N-formyl-L-alanyl]-3-[m-bis(2-chloroethyl)aminophenyl]-L-alanyl]-L-methionine ethyl ester. Tripeptide III by Reaction III

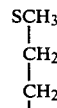
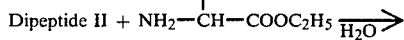

-continued

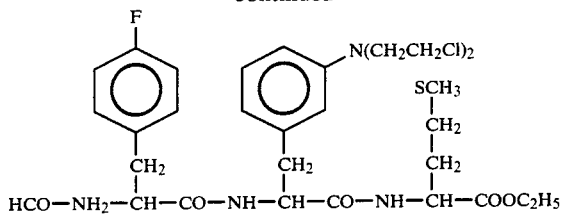

Dipeptide II (27.7 g) derived from reaction II was dissolved in 225 ml of N,N-dimethylformamide at 40° C. After cooling it to 15° C., a solution of L-methionine ethyl ester [10.28 g] in 20 ml of N,N-dimethylformamide was added, followed by successive addition of N-hydroxysuccinimide [8.6 g] and N,N-dicyclohexylcarbodiimide [12.57 g] in 25 ml of N,N-dimethylformamide. The thus obtained mixture was kept at 5° C. for 30 minutes while stirring. Then the temperature was allowed to rise to 20° C. and the mixture was agitated for 20 hours at 20° C. Dicyclohexylurea was removed by filtration, and to the filtrate while stirring, 1800 ml of water was added at 15° C. After washing, the filtrate was air dried and then successively kept under vacuum in the presence of P$_2$O at 40° C. Purification of crude substance was achieved by suspending it in 120 ml absolute ethyl alcohol and solubilized by adding small portions of N,N-dimethylformamide and suspended for 15 hours at 5° C. The crystalline product was filtered and washed with absolute ethyl alcohol and dried under vacuum at 40° C. The white crystalline substance, Tripeptide III, had the following properties: MP 187°-189° C., an analysis showing the compound C$_{30}$H$_{39}$FCl$_2$N$_4$O$_5$S (M=657.64), with-calculated composition (%) C 54.79—H 5.98—N 8.51—Cl 10.78—S 4.87. Found (%): C 54.03—H 5.89—N 8.52—Cl 10.71—S 4.84.

Synthesis of N-[N-[3-(p-fluorophenyl)-L-alanyl]-3-[m-bis(2-chloroethyl)aminophenyl]-L-alanyl]-L-methionine ethyl ester HCl. Tripeptide salt III by Reaction IV

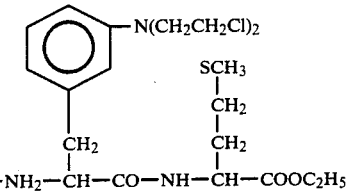

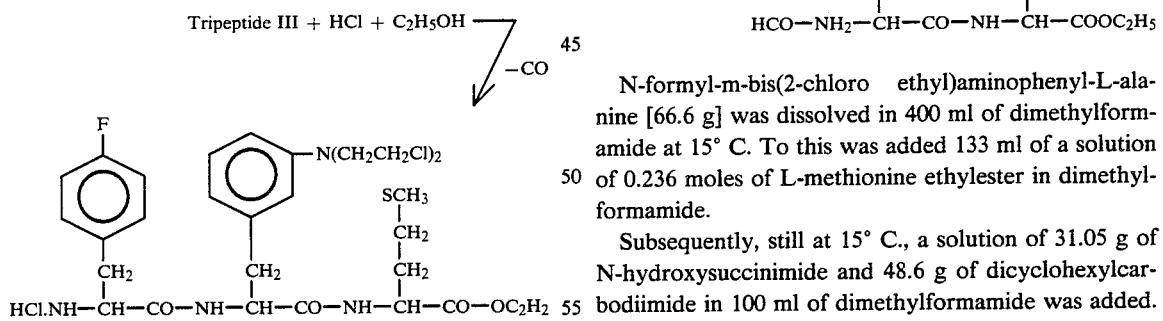

Tripeptide III [17.75 g] from reaction III was suspended in 250 ml HCl solution (4.1% w/v) in absolute ethyl alcohol was stirred for 4 hours at 20° C. The reaction mixture was held for 15 hours at 5° C. The course of hydrolysis reaction was monitored with TLC using ethyl ester/acetic acid/water=135:27:9 (v/v/v) solvent system. At the completion of the reaction, to the resulting clear solution 250 ml of water were slowly added while stirring and maintaining the pH at 3-3.2 with NaHCO$_3$ at 5° C. After 20 minutes agitation, the white bulky substance was filtered followed by washing with cold water at 5° C. The sample was first air dried, then vacuum dried at 40° C. in presence of P$_2$O$_5$. Purification of the crude product was performed. Crystallization in isopropyl alcohol at 60°-65° C. was conducted after which the product in the isopropyl alcohol was cooled for 16 hours, at 15° C., filtered, washed first with isopropanol then with acetone and dried under vacuum at 40° C. for 8 hours. The analysis of the resulting white crystalline substance (the tripeptide salt) showed the following characteristics MP 180°-182° C.; Analysis: for C$_{29}$H$_{39}$Cl$_2$FN$_4$O$_4$SHCl (MW=666.08); Calculated %: C 52.29—H 6.05—N 8.41—Cl 15.97—S 4.81; Found %: C 52.31—H 6.09—H 8.38—CL 15.85—S 4.76.

Example No. 2

Synthesis of N-formyl-m-bis(2-chloroethyl)aminophenyl-L-alanyl-L-methionine ethyl ester. Dipeptide I by Reaction I

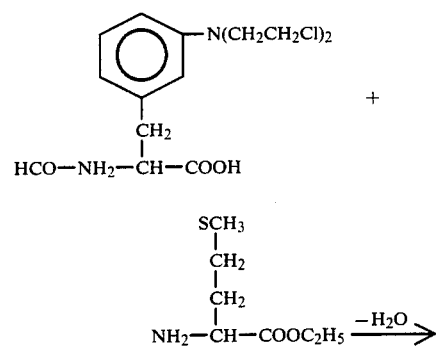

N-formyl-m-bis(2-chloro ethyl)aminophenyl-L-alanine [66.6 g] was dissolved in 400 ml of dimethylformamide at 15° C. To this was added 133 ml of a solution of 0.236 moles of L-methionine ethylester in dimethylformamide.

Subsequently, still at 15° C., a solution of 31.05 g of N-hydroxysuccinimide and 48.6 g of dicyclohexylcarbodiimide in 100 ml of dimethylformamide was added.

After 18 hours of agitation at room temperature, the dicyclohexylurea was removed by filtration and washed on the filter with 2×30 ml of dimethylformamide. Two liters of an ice-water was added to the filtrate under agitation at a rate such as to maintain the temperature below 20° C.

A white precipitate was collected on the filter, washed with water and dried under vacuum at 40° C. Yield: 90.5 g (92%) with a melting point of 93°-95° C.

Analysis: N=8.49% (calculated 8.53%). Cl=14.44% (calculated 14.41%). S=6.51% (calculated 6.52%).

Synthesis of m-bis(2-chloroethyl)aminophenyl-L-alanyl-L-methionine ethyl ester hydrochloride. Dipeptide II by Reaction II Dipeptide I + HCl + $C_2H_5OH \xrightarrow[-CO]{}$ $$\underset{\underset{HCl.NH_2-CH-CO-NH-CH-COOC_2H_5}{|}}{\underset{|}{CH}\text{-Ar-}N(CH_2CH_2Cl)_2} \quad \underset{|}{\underset{CH_2}{SCH_3}}$$

To 600 ml of a 1.5 N solution of HCl in anhydrous ethyl alcohol was added 49.2 g of Dipeptide I from Reaction I. The solution was retained in a flask for 6 hours.

After a chromatographic check (TLC) had revealed the absence of the initial product, the solution was evaporated under reduced pressure at 40° C. until an oily residue was left.

The residue was taken up with 150 ml of cold water (at +5° C.) and a whitish product separated which was dispersed under agitation for 15 minutes; the pH was brought to 3.5 by the addition of an aqueous 10% sodium bicarbonate solution.

The product was collected by filtration, and washed on the filter with cold water. It was dried under vacuum at 40° C. over $P_2O_5$.

Yield: 41.8 g (88.5%) with a melting point of 135°–138° C.

Analysis: N=8.79% (calculated 8.88%). Cl=7.51% (calculated 7.50%). S=6.77% (calculated 6.78%). $Cl_2$=22.39% (calculated 22.79%).

Synthesis of m-bis(2-chloroethyl)-aminophenyl-L-alanyl-L-methionine ethyl ester. Dipeptide III by Reaction III Dipeptide II + $H_2O \longrightarrow$ $$\underset{NH_2-CH-CO-NH-CH-COOC_2H_5}{\text{Ar-}N(CH_2CH_2Cl)_2, SCH_3, CH_2, CH_2, CH_2}$$

To 41.8 g of Dipeptide II from Reaction II was added 120 ml of chloroform and 100 ml of an aqueous 10% $NaHCO_3$ solution. The mixture was agitated for 15 minutes at 5° C.

The chloroform phase was separated, washed with water, dried, filtered and evaporated under reduced pressure at 40° C.

The oily residue was taken up with 150 ml of tetrahydrofuran.

The solution was titrated potentiometrically with 0.1N $HClO_4$ in acetic acid. There were 0.083 moles of the dipeptide in the solution.

Synthesis of N-[N-[3(p-fluorophenyl)-L-alanyl]-3-[m-bis(2-chloroethyl)aminophenyl]-L-alanyl]-L-methionine ethyl ester HCl. Tripeptide I by Reaction IV Dipeptide III +

$$\text{F-Ar-}CH_2\text{, Ar-}N(CH_2CH_2Cl)_2, SCH_3, CH_2, CH_2, CH_2$$
$$HCl.NH_2-CH_2-CO-NH-CH-CO-NH-CH-COOC_2H_5$$

$\uparrow$

F-Ar-$CH_2$
HCO—$NH_2$—CH—COOH + HCl

To a solution of 17.5 g of N-formyl-p-fluorophenyl-L-alanine in 180 ml of tetrahydrofuran was added the dipeptide III and 18.5 g of dicyclohexylcarbodiimide. Agitation was maintained for 6 hours and the couse of the reaction was checked by TLC.

The dicyclohexylurea was removed by filtration and the filtrate was poured into 1800 ml of cold water (+5° C.). The suspension was brought to a pH of 3.5 with 2N HCl and, after 15 minutes of agitation under cold conditions, the voluminous white product was collected by filtration and washed on the filter with cold water. The product was dried under vacuum at 40° C. over $P_2O_5$.

Yield: 45.8 g (83%) with a melting point of 180°–182° C.

Analysis: N=8.40% (calculated 8.41%). Cl=5.33% (calculated 5.32%). $Cl_2$=15.89% (calculated 15.97%). S=4.82% (calculated 4.81%).

The tripeptide compound can be administered intravenously (preferred) or orally (not preferred) in a suited pharmaceutical form, as for example, solutions in anhydrous solvents diluted immediately before use with injectable sterile 5% glucose solution.

Fluid unit dosage forms for parenteral (i.e. intravenous) administration can be prepared by dissolving a measured amount of the compound in a non-toxic liquid vehicle. For example, 1–4 g (according to the dosage suggested by biological and clinical assays) of the tripeptide compound is dissolved in 60 ml of a solvent mix consisting of 25% dimethylacetamide, 50% propylene glycol, and 25% of an emulsifier, such as for example, Tween 80. When all of the tripeptide is dissolved, the solvent mix is added until a volume of 100 ml is achieved. The solution is sterilized by sterilizing filtration, then is distributed in 1 ml amber glass ampoules, performing all the operations under sterile conditions and in a nitrogen atmosphere. Before use, the 1 ml ampoule must be mixed with 100–200 ml of a sterile 5% glucose solution.

Many factors which modify the action of the tripeptide compound will be taken into account by those skilled in the art, for example, age, body weight, sex, diet, time of administration, route of administration, rate of metabolism or excretion, drug combination, sensitivities and severity or condition of the disease. Optimal application dosages for a given set of conditions can be ascertained by those skilled in the art using conventional tests for the unit dosages determined in view of the above guidelines.

Preferably, the tripeptide compound will be administered intravenously: injection solutions contain 20–200 ug of the tripeptide compound per ml of the pharmaceutical carrier.

The chemotherapeutical activity of the compounds (tripeptides) of the present invention toward tumors was evaluated experimentally by means of determation of the mean survival time.

Determination of the mean survival time (mean survivial time=MST) of $BDF_1$ mice, inoculated intraperitoneally with $10^5$–$10^6$ cells of lymphatic leukemia L-1210 taken from regular implants in DEA2 mice was calculated. The MST of both the control and of the treated mice was determined, and then the increased lifespan (ILS) was determined as set out in "Cancer Chemotherapy Reports", 1972, vol. 3, no. 2 (Protocols for Screening Chemical Agents and Natural Products)—Against Animal Tumors And Other Biological System—third Edition, National Cancer Inst. Bethesda Md. The compounds were tested by injection intraperitoneally or subcutaneously 24 or 48 hours after the tumor inoculum either in a single massive dose or with fractions of the dose at intervals of 8 days, progressively reduced.

TEST NO. 1

Toxicity Test

Male and Female albino mice of the Swiss strain (Morini) having an average weight of 21 g, and male and female albino rats of the Wistar strain (Morini) having an average weight of 100–150 g were employed. All were kept fasting for 12 hours before the tests. A weighted quantity of the tripeptide salt from 1 to 4 g (according to the dose suggested by biological and clinical assays) is dissolved in 60 ml of a solvent mix made up by 25% dimethylacetamide, 50% propylene glycol and 25% Tween 80. Gently warm at 40° C. for no more than a few minutes, then maintain under agitation in a nitrogen atmosphere until all the material is dissolved.

Bring the volume to 100 ml with the afore described solvent mix. Filter through millipore sterilizing filter and then distribute in 1 ml amber glass ampoules, performing all the operations under sterile conditions and in a nitrogen atmosphere. Before use, 1 ml of such solution is mixed with 100 or 200 ml of sterile 5% glucose solution. Dosages of 5 and 10, 20, 30, 40, etc. mg per kg of animal weight were both intravenously and intraperitoneally administered for both the mice and the rats. Toxic effects and mortality were checked for a month after treatment. The amount of drug which induced death in 50% of the test animals ($LD_{50}$) was determined by the Litchfield and Wilcoxon method. (See Table 1)

TABLE 1

TOXICITY OF THE TRIPEPTIDE OF EXAMPLE 1 $LD_{50}$ IN THE MOUSE AND IN THE RAT AFTER I.V. AND I.P. ADMINISTRATION

| TEST ANIMAL | ROUTE OF ADMINISTRATION | SLX | $LD_{50}$ mg/kg | FIDUCIAL (P = 0.05) |
|---|---|---|---|---|
| mouse | I.V. | m | 17.0 | 12.9–22.4 |
|  |  | f | 38.1 | 32.4–44.9 |
|  | I.P. | m | 20.7 | 17.6–24.5 |
|  |  | f | 38.1 | 32.4–44.9 |
| rat | I.V. | m | 9.3 | 7.8–10.9 |
|  |  | f | 17.3 | 15.7–19.1 |
|  | I.P. | m | 9.2 | 7.1–11.9 |
|  |  | f | 18.2 | 14.5–22.9 |

The maximum dosage of solvent administered to both the rats and the mice by either intravenously or intraperitoneally caused no mortalities. The intravenous 50% death rate in mice was 17.0 mg per kg in male and 38.1 mg per kg in females. The intraperitoneal 50% death rate in mice was 20.7 and 38.1 mg per kg in males and females respectively. The intravenous 50% death rate in rats was 9.3 mg per kg in males and 17.3 mg per kg in females. The intraperitoneal 50% death rates in rats was 9.2 and 18.2 mg per kg in males and females respectively. Clearly there is a sharp difference in toxicity between males and females. The animals showed a normal behavior for two days after administration, although during this time period they ate less than usual. On the third day all animals treated with high dosages showed a strong piloerection, breathing difficulties, and loss of weight. After 72 hours the first deaths occured. Most of the deaths happened between the fourth and seventh days, whereas the last were observed on the fifteenth day. The microscopic examination showed congested viscera with peritoneal liquid; the stomach was swollen, the duodenum and part of the small intestines were full of a yellowish liquid, the liver was enlarged and hard, whereas the spleen was small. All surviving animals recovered their normal appearance and behavior about three weeks after treatment.

TEST NO. 2

Activity on Leukemia L-1210

Male mice (DBA/2) were innoculated intraperitoneally on day 0 with $10^6$ untreated leukemia L-1210 cells. The innoculated tumor bearing mice were treated 48 hours later with a single dose of 5, 7.5, 10, 15, or 20 mg of the tripeptide salt of Example 1 per kg of animal weight, intraperitoneally. The data from this test is set forth in Table 2. The optimal therapeutic dose appears to be approximately 10 mg per kg as a single dose, resulting in an increase of the mean survival time (MST) from 8.2 days to 28 days with an increased life span (ILS) of 216.5%, and an apparent cure of 15% of all such treated animals. The concentration of the tripeptide salt of Example 1 in amounts above 15 mg per kg was toxic to treated mice and all died tumor free 3 to 5 days after the onset of treatment.

TEST NO. 3

Activity on Leukemia in AKR mice

AKR mice are used as a model for human leukemias in studies in chemotherapy. Leukemia in AKR mice mimics human leukemias in many respects and it is probable that the AKR leukemia is analogous to human acute T-cell lymphocytic leukemia. Leukemic cells first appear in the thymus of mice 6 to 12 months of age. The time lapse between the first appearance of viable Lymphoma cells in the thymus and the clinical diagnosis is about 30 days. The clinical diagnosis of spontaneous leukemia in AKR mice was made with 95% accuracy by splenic and lymph node palpation, followed by leukocyte count.

TABLE 2

CHEMOTHERAPEUTIC ACTIVITY OF THE SYNTHETIC TRIPEPTIDE OF EXAMPLE 1 IN MICE WITH SPONTANEOUS OR TRANSPLANTABLE LEUKEMIA

| Study Groups | Day (s) Treatment | Dose[1] mg/kg | MST in days | ILS in Percent | Weight Change[2] in Percent |
|---|---|---|---|---|---|
| DBA/2 | Control | 0 | 8.2 + 1 | — | — |
| Mice | 2 | 5 | 14.0 + 2.2 | 70.7 | −2.5 |
| with | 2 | 7.5 | 18.0 + 3.1 | 119.5 | −3.2 |
| L1210 | 2 | 10.0 | 28.0 + 4.2 | 241.5 | −4.1 |
| leukemia | 2 | 15.0 | 8.0 + 1.6 | 0 | −11.9 |
|  | 2 | 20.0 | 5.0 + 1.4 | 0 | −6.7 |
| AKR | Control | 0 | 14.6 + 3.8 | — | — |
| mice | 1 | 5 | 17.9 + 5.3 | 22.6 | −1.2 |
| with | 1 | 7.5 | 21.8 + 5.0 | 49.3 | −2.4 |
| spontane- | 1 | 10 | 28.5 + 4.9 | 95.2 | −4.5 |
| ous leu- | 1 | 15 | 16.9 + 6.1 | 15.8 | −10.3 |
| kemia* | 1,4,7 and 21 | 5 | 49.5 + 5.7 | 239.0 | −3.8 |
|  | 1 and 14 | 10 and 5 | 41.0 + 6.3 | 180.8 | 8.2 |

*Treatment was initiated after clinical diagnosis of leukemia
[1]intraperitoneally [i.p.]
[2]Recorded on day 8 after first dose as compared to body weight observed before therapy In an attempt to achieve remission, induction with the tripeptide of Example 1 was used; as a single dose 5, 7.5, 10, and 15 mg per kg of the tripeptide was employed; or for a multiple dose treatment 5 mg per kg administered intraperitoneally on days 1, 4, 7, and 21; or 10 mg per kg administered intraperitoneally on day 1 and 5 mg per kg administered intraperitoneally on day 14. The mean survival time and the increased life span were determined for the AKR mice (see Table 2).

AKR mice die after diagnosis of spontaneous leukemia at the rate of 50% by 14 days, 90% by 33 days, and 96% by 56 days. In our preliminary study, excellent remission induction was achieved with the tripeptide of Example 1 administered at 10 mg per kg on days 1 and 14; and 5 mg per kg on days 1, 4, 7, and 21, and 42.

These leukemic AKR mice sustained an increased life span at 180% and 239%, respectively. It is noted that the tripeptide treatment provided good sustainment of remission since 30% of the treated animals in either group were alive 80 days after therapy.

What is claimed is:

1. A pharmaceutical composition comprising:
   (a) an effective amount of a tripeptide compound, said tripeptide compound being a member selected from the group consisting of:
      (i) 3-(p-fluorophenyl)-L-alanyl-3(m-bis(2-chloroethyl)-aminophenyl)-L-alanyl-L-methionine;
      (ii) 3-(m-bis(2-chloroethyl)aminophenyl)-L-alanyl-3-(p-fluorophenyl)-L-alanyl-L-methionine;
      (iii) 3-(p-fluorophenyl)-L-alanyl-L-methionyl-3-(m-bis(2-chloroethyl)aminophenyl)-L-alanine;
      (iv) 3-(m-bis(2-chloroethyl)aminophenyl)-L-alanyl-L-methionyl-3-(p-fluorophenyl)-L-alanine;
      (v) L-methionyl-3-(p-fluorophenyl)-L-alanyl-3-(m-bis(2-chloroethyl)aminophenyl)-L-alanine;
      (vi) L-methionly-3-(m-bis(2-chloroethyl)aminophenyl)-L-alanyl-3-(p-fluorophenyl)-L-alanine; and
   (b) a pharmaceutically acceptable excipient for treatment of malignant tumor cells in laboratory animals.

2. The pharmaceutical composition of claim 1, wherein said excipient comprises a solvent mixture of dimethylacetamide, propylene glycol, and an emulsifier in an aqueous solution.

3. The pharmaceutical composition of claim 2, wherein said aqueous solution is 5% dextrose in water.

4. The pharmaceutical composition of claim 1, wherein said effective amount of said tripeptide compound is less than 15 milligrams per kilograms of laboratory animal weight to be treated for said malignant tumor cells.

5. The pharmaceutical composition of claim 1, wherein said effective amount of said tripeptide compound is between about 5 milligrams to about 15 milligrams per kilogram of laboratory animal weight to be treated for said malignant tumor cells.

* * * * *